United States Patent [19]

La Gro

[11] Patent Number: 5,593,397
[45] Date of Patent: Jan. 14, 1997

[54] FECAL COLLECTOR WITH ELASTIC ATTACHMENT PATCH

[75] Inventor: Phillip A. La Gro, Hawthorn Woods, Ill.

[73] Assignee: Hollister Incorporated, Libertyville, Ill.

[21] Appl. No.: 501,774

[22] Filed: Jul. 13, 1995

[51] Int. Cl.$^6$ ........................................... A61F 5/44
[52] U.S. Cl. ........................... 604/355; 604/332; 604/349
[58] Field of Search ..................................... 604/327, 332, 604/339, 341, 342, 355

[56] References Cited

U.S. PATENT DOCUMENTS

| | | | |
|---|---|---|---|
| 3,522,807 | 8/1970 | Millenbach | 604/355 |
| 3,804,093 | 4/1974 | Fell | 128/286 |
| 4,368,733 | 1/1983 | Sanidas | 128/283 |
| 4,445,898 | 5/1984 | Jensen | 604/337 |
| 4,465,486 | 8/1984 | Hill | 604/341 |
| 4,850,986 | 7/1989 | Temple | 604/355 |
| 5,312,384 | 5/1994 | Temple | 604/355 |
| 5,417,677 | 5/1995 | Schneider | 604/332 |

*Primary Examiner*—John G. Weiss
*Assistant Examiner*—David J. Cho

*Attorney, Agent, or Firm*—Tilton, Fallon, Lungmus

[57] ABSTRACT

The fecal collector that includes a bag of elastomeric heat-sealable film having an opening for receiving fecal discharge and a thin attachment patch having a central opening in register with the opening of the bag. The patch includes a skin barrier layer of rubbery pressure-sensitive adhesive having hydrocolloid particles dispersed therein and having a backing layer secured to one side of the skin barrier layer. The backing layer is formed of stretchable and contractable heat-sealable material and is joined to the bag along a narrow annular heat seal line immediately surrounding the openings of the bag and patch. Because of the elastic properties of the materials, the openings may readily expand and contract to accommodate anatomical changes commonly occuring during defecation, thereby preventing disruption of the adhesive attachment between the patch and the patient. The backing layer of the patch is provided with a tab portion extending outwardly beyond the skin barrier layer to facilitate later removal of the patch from the patient's skin, such tab portion overlying a similar tab portion extending from a removable release sheet that protects the opposite side of the skin barrier layer prior to adhesive attachment of the patch to the patient. The patch also includes a removable perineal section that may be cut from the patch as delineated by guidelines imprinted on the release sheet.

4 Claims, 2 Drawing Sheets

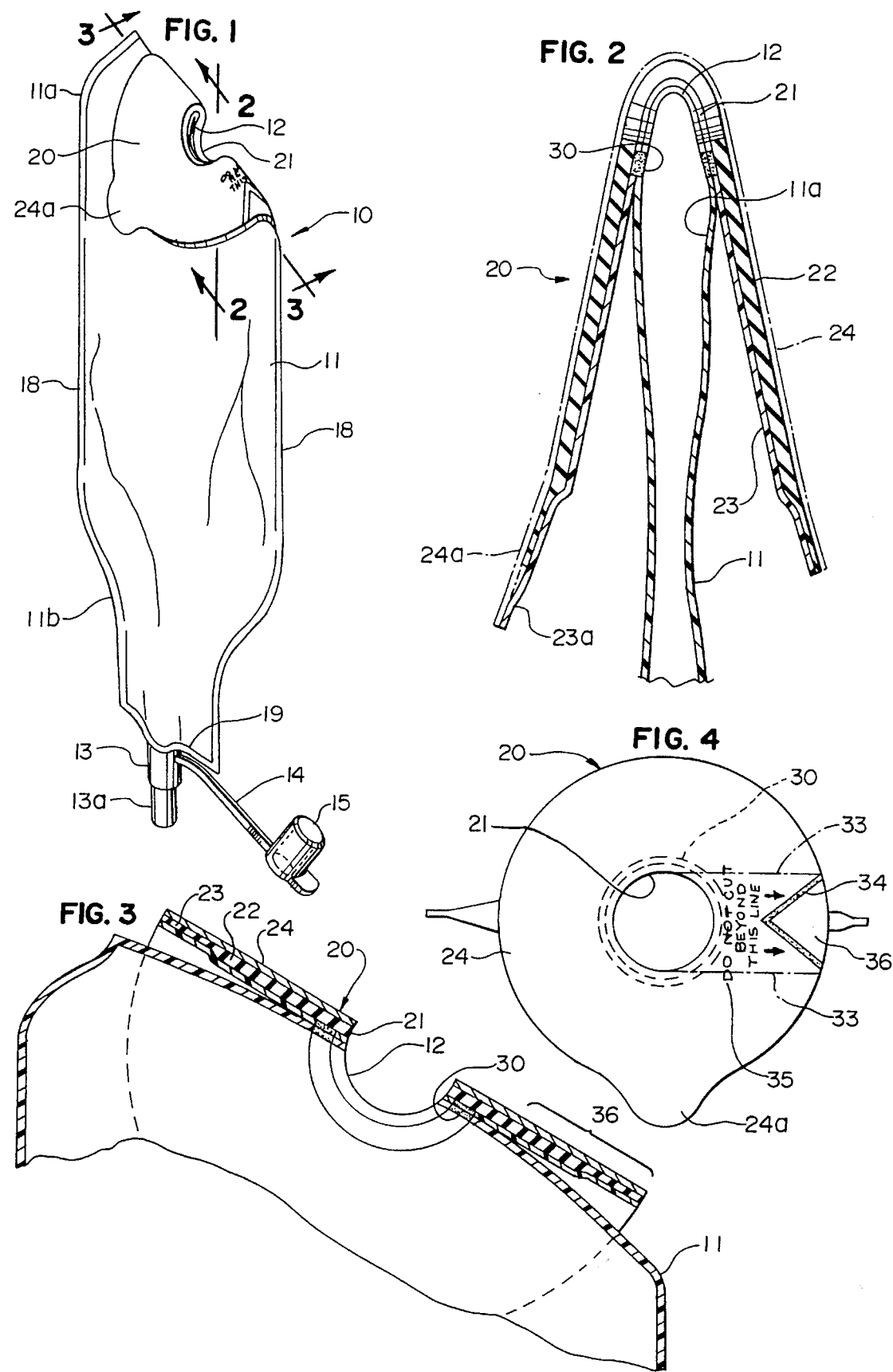

FECAL COLLECTOR WITH ELASTIC ATTACHMENT PATCH

BACKGROUND

Jensen U.S. Pat. No. 4,445,898 discloses a fecal incontinence device in the form of a collection bag joined to an adhesive attachment ring 12 along a heat seal line 32a extending about a large opening 29. The opening is off-center to provide the ring with a relatively narrow perineal portion 26a. Similar incontinence devices have been marketed with starter openings of smaller size than shown in the patent (such openings may be enlarged by a user or nurse, using scissors, prior to adhesive attachment of the ring to the perineal surfaces), but such starter openings have been of even greater eccentricity in order to maintain the relatively narrow radial dimensions of the perineal portion 26a. In both constructions, the annular heat seals between the bags and the attachment rings have been located near the outer margin of the rings, or at least closer to those outer margins than to the rings' centers.

While a heat seal nearer the outer margin of an attachment ring allows for a relatively large opening, (or one that may be cut to a larger size at the time of application), it is now believed that locating the heat seal near an outer margin increases the risk that forces exerted on a collection bag are more likely to result in unintentional detachment of the adhesive ring from a patient when the device is in use. Should pulling forces be exerted on the bag—for example, when a bedridden patient rolls or moves about—the concentration of those forces at one or more points along the outer margin of the attachment ring may cause the ring to peel away from the skin.

Temple U.S. Pat. No. 4,850,986 discloses an incontinence device in the form of a latex tube having a tapered end portion 28 terminating in an opening and coated about that opening with a suitable pressure-sensitive adhesive 27. An applicator must be used to bring the adhesive coating of the conical portion into contact with the perianal surfaces at the time of application.

Other patents illustrative of the prior art on fecal collectors adapted for perianal attachment are Fell U.S. Pat. Nos. 3,804,093, Sanidas 4,368,733, Millenbach 3,522,807, and Temple 5,312,384.

SUMMARY OF THE INVENTION

One aspect of this invention lies in the discovery that the aforementioned disadvantages of heat sealing a bag and an attachment patch together near the outer margin of such a patch may be avoided by relocating the heat seal radially inwardly and, at the same time, forming the patch and bag of materials having elastomeric properties, and in the further discovery that in such a construction it is unnecessary to provide a large opening in the patch, or one that may be manually enlarged at the time of application. Specifically, a patch having an opening of about one inch in diameter, or one generally within the range of about 0.5 to 1.5 inches in diameter, will be highly effective if the materials of the patch and bag are sufficiently stretchable and recoverable to remain attached to the perianal surfaces even though those surfaces enlarge, contract, and dramatically change in contour during normal evacuation. The bag and attachment patch should be secured together along a narrow annular heat seal line located in close proximity to the edges of the openings in the patch and bag, leaving a large area of the patch beyond the seal line free for adhesive attachment to a wearer. More specifically, at least 80 percent and preferably 90 percent or more of the adhesive surface area of the patch should be disposed outboard of the annular heat seal line.

The opening in the patch should also be centrally located to insure large areas of adhesive attachment to the perineal, coccygeal, and other portions of the perianal surface. In that connection, it is now recognized that only a relatively small proportion of female patients have perineal dimensions (rectum to vaginal introitus) that might require some reduction in the radial dimension of the perineal portion of an adhesive patch. An aspect of this invention lies in recognizing that such reduction may be easily achieved by removing a section of the patch extending inwardly a limited distance from the patch's outer margin.

Briefly, a fecal collector embodying this invention takes the form of a bag of elastomeric heat-sealable film having an opening for receiving fecal discharge, and a thin annular attachment patch having a central opening in register with the opening of the bag. The patch comprises a skin barrier layer of rubbery pressure-sensitive adhesive having liquid-absorbing hydrocolloid particles dispersed therein and having a backing layer secured to one side of the skin barrier layer. The backing layer is formed of stretchable and contractable heat-sealable material that is preferably porous, the backing layer being joined to the bag along a narrow annular heat seal line immediately surrounding the openings of the bag and patch. Because of the stretchable and contractable qualities of the bag and patch, the collector is well adapted to remain adhesively attached to the perianal surfaces as those surfaces enlarge, contract, and dramatically change in contour during evacuation. The bag and patch openings, and the heat sealed connection about those openings, also expand and contract as such anatomical changes occur.

Prior to use, the adhesive surface of the patch is covered by a removable release sheet that preferably has a tab projecting outwardly beyond the outer margin of the skin barrier layer to facilitate removal of the release sheet at the time of application. Of particular importance is the fact that the backing layer is also provided with a tab portion that projects beyond the outer margin of the barrier layer (and preferably underlies the tab portion of the release sheet). Since the tab portion of the backing layer has no adhesive coating or layer, it remains unattached to the patient's skin when the collector is worn. The backing layer's tab portion may be easily grasped to peel away the entire adhesive patch from the patient when removal of the collector is desired.

For those female patients requiring a patch with a perineal portion of reduced size, guidelines are provided on the release sheet defining the maximum limits of a removable portion, some or all of which may be cut away by the caregiver just prior to application to a patient. Suitable instructions may also be imprinted on the release sheet to insure that a user does not remove an excessively large section or segment from the periphery of the attachment patch.

DRAWINGS

FIG. 1 is perspective view of a fecal collector embodying this invention.

FIG. 2 is an enlarged fragmentary sectional view taken along line 2—2 of FIG. 1.

FIG. 3 is a sectional view along line 3—3 of FIG. 1.

FIG. 4 depicts the attachment patch of the collector in planar condition.

DETAILED DESCRIPTION OF PREFERRED EMBODIMENTS

Figure 5:
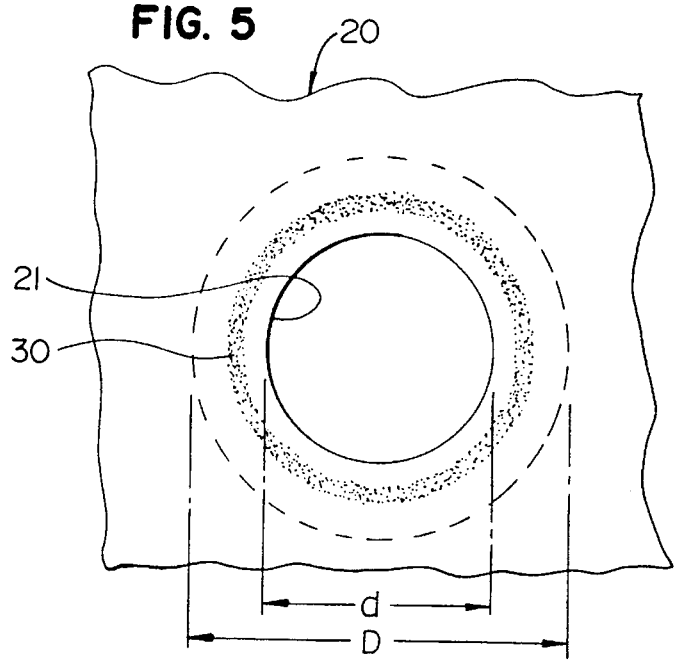
FIG. 5 is a fragmentary and somewhat schematic view of the patch and its heat-sealed connection to the bag showing the dimensional changes that may occur in and about the openings of the patch and bag when outward forces are exterted to enlarge the size of such openings.

Referring to the drawings, fecal collector 10 takes the form of an enlonged bag 11 having an opening 12 at one end 11a. The opposite end 11b is provided with a closable drain 13 in the form of a plastic tube 13a heat sealed or otherwise attached to the thermoplastic film of the bag. An integral strap 14 joins the tube 13a to a closure cap 15 that may be fitted over the end of tube 13a to seal the pouch's lower end. While it is preferable to provide such a drain at the lower end of the pouch, it is to be understood that such drain may be omitted if desired.

The bag may be formed from a single sheet of heat-sealable film folded at its upper end 11a as indicated in FIGS. 1 and 2 with the side panels then heat sealed together along their side and bottom edges as indicated at 18 and 19 in FIG. 1.

The bag may be formed of any heat-sealable film that has elastomeric properties and is tough and lightweight. Silicone rubber films, polyurethane films, and other elastomeric films might be used effectively. A particularly suitable material having sufficient stretchability and recoverability for this application is believed to be a copolymer of ethylene and vinyl acetate (EVA) blended with polyethylene and marketed under the designation EA 8 by Film Tech Corp., Stanley, Wis.

The attachment patch 20 is generally circular in outline and has a central opening 21 corresponding in size and shape, and registering with, bag opening 12. The patch is planar at the time of manufacture and may be easily folded for application to the patient as depicted in FIGS. 1 and 2.

The patch essentially consists of a skin barrier layer 22 covered on one side by a backing layer 23 and on its other side by a removable release layer 24. The skin barrier layer may be composed of any of a variety of known skin barrier materials in which there is a continuous phase of a rubbery adhesive material having a discontinuous phase in the form of hydrocolloid particles dispersed throughout. Ideally, the continuous phase is composed at least in part of a styrene-isoprene-styrene block copolymer such as "CARIFLEX" TR-1107 (Shell Chemical Co.) or a styrene-butadiene-styrene block copolymer such as "KRATON" 101 (Shell Chemical Co.). Other elastomeric A-B-A block copolymers, such as ethylene-propylene block copolymers known as EPR rubbers are also believed suitable. The gel-like composition may also include other adhesive elastomers in the continuous phase, polyisobutylene being particularly effective for that purpose. Plasticizers such as mineral oil or petrolatum and suitable tackifiers and antioxidants, all as well known in the art, may also be included in the continuous phase.

The discontinuous phase may be particles of any suitable hydrocolloid or mixtures of hydrocolloids such as sodium carboxymethylcellulose, pectin, gelatin, and natural gums such as gum guar, gum arabic, locust bean gum, karaya and the like. The hydrocolloid is water-absorbing and water-swellable. It absorbs moisture from the skin and contributes to the wet tack characteristics of the skin barrier material, all as well known in the art.

While any of a number of known skin barrier materials having elastomeric properties may be used, a particularly effective material for that purpose is disclosed in copending application 223,649, filed Apr. 6, 1994. Other materials, such as those disclosed in U.S. Pat. No. 4,231,369, are believed suitable.

Backing layer 23 must be heat-sealable, stretchable, and recoverable. It may take the form of a film of polyurethane or other elastomeric material, but a preferred material is a nonwoven microporous fabric composed of polyethylene fibers such as for example, microporous fabric marketed under the designation MF 5260 by Freudenberg Nonwovens LP, Halifax, England. Such material is soft, conformable, and sufficiently stretchable and recoverable to expand, contract, and deform to follow changes in body contour when the patch is adhesively secured to a patient in the perianal area. Other pliant heat-sealable materials having similar properties, whether microporous or not, may also be used.

The adhesiveness of the barrier layer 22 securely bonds layers 22 and 23 together to provide a laminated patch capable of stretching, contracting and conforming to match the anatomical changes occurring in the perianal area to which the patch is secured in use. The outside diameter of the patch may fall generally within the range of about 2.5 to 5 inches with a preferred range being approximately 3 to 4 inches. The central opening 21 of the patch, as well as the matching opening 12 of the bag, should have a diameter within the range of about 0.5 to 1.5 inches, with the optimum diameter believed to be about 1 inch. The release sheet 24 may be formed of any sheet material that resists secure attachment to the adhesive surface of barrier layer 22. Ideally, such a sheet material is relatively non-stretchable, such as paper having a siliconized surface in releasable contact with the adhesive barrier layer.

The attachment patch 20 is secured to the bag by a narrow annular heat seal zone or line 30 extending about and immediately adjacent the aligned openings 12 and 21 of the bag and patch. It is important that seal line 30 be located in close proximity to the opening, leaving as much area as possible of the patch outboard of that line free for attachment to the patient's skin. At least 80 percent of the surface area of the patch should be disposed outboard of the annular seal line. Preferably 90 percent or more of the patch's surface area is so disposed. For example, for a patch having an outside diameter of about 3.6 inches and an opening diameter of about 1 inch, the proportion of adhesive surface area outboard of the seal line may be 92 percent or more.

The radially inward location of the heat seal line in close proximity to central openings 12, 21 prevents the weight of the bag and its contents from exerting pulling forces on the outer periphery of the patch when the collector is in use, thereby reducing the possibility that the appliance might become detached from the patient's skin. Such location of the heat seal also leaves the major area of the faceplate free to conform to the patient's anatomy without interference from the bag. This is particularly important where, as here, the patch is stretchable and contractable, since the flexing, stretching and contracting of the major areas of the patch outboard of the seal line 30 may occur without restraint by or involvement from the bag.

During evacuation, considerable stretching of the patch and bag may occur in the annular area immediately surrounding openings 12, 21—that is, in the region of heat seal 30. FIG. 5 schematically depicts the changes that could occur in that region. The unstretched diameter of patch opening 21 (also bag opening 12) is represented as "d" whereas an expanded diameter that might be attained during normal evacuation, considering the age, physical condition, and medical treatment of patients with which such collection devices are commonly used, is given as "D". In the illustration given, D is 75% greater than d, resulting in an opening which has an area approximately 206% greater than the smaller opening.

The following example concerning the expandability and recoverability at the opening of a collector made in accordance with this disclosure is further illustrative of the invention:

EXAMPLE

Thirty collectors of identical construction having the appearance depicted in FIG. 1 were tested to determine the ease with which the collector openings could be expanded to different diameters and the extent of recovery following such expansion. Each collector included a pouch formed of a 2.1 mil film of a copolymer of ethylene and vinyl acetate blended with polyethylene and marketed under the designation EA 8 (Film Tech Corp.). The attachment patch of each collector had an outside diameter of 3.625 inches (exclusive of tab 24a) and a central opening of 1.0 inches in diameter in an unstretched state. The pouch opening was of the same diameter, and the two components were heat sealed together along a heat seal line having an inside diameter of 1.125 inches and a width of 0.125 inches.

Each attachment patch was composed of two layers (exclusive of release paper), one layer being a skin barrier layer of "FLEXTEND," an elastomeric hydrocolloid-containing skin barrier material marketed by Hollister Incorporated, Libertyville, Illinois. The barrier layer was of a thickness of 0.04 inches extending outwardly from the central opening, and such thickness was constant except for an annular outer rim of 0.02 inches in thickness, and a width of 0.4375 inches, extending along the extreme outer limits of the patch. The layer of the patch heat-sealed to the pouch was a nonwoven microporous fabric of 0.013 inches in thickness composed of polyethylene fibers and marketed under the designation MF 5260, Freudenberg Nonwovens LP.

The 30 collectors had their pouches cut outboard of the patches so that the patches could be laid flat and the openings were accessible from both sides. A testing mandrel of frusto-conical shape was prepared, the mandrel having a reduced end of 1.0 inches in diameter, an enlarged end exceeding 1.75 inches in diameter, and a straight uniform taper of 7 degrees measured from the mandrel's longitudinal axis. The tapered surface of the mandrel was calibrated at diameters of 1.25 inches (diameter increase from reduced end, 25%; area increase 56%), 1.50 inches (diameter increase 50%; area increase 125%), and 1.75 inches (diameter increase 75%; area increase 206%).

The testing procedure involved the use of an Instron Series IX Automated Materials Testing System 065 which measured the force required to advance each pouch with its opening fitted upon the reduced end of the mandrel and advanced at a crosshead speed of 3 inches per minute to a selected calibration mark along the mandrel's tapered surface. Ten of the 30 collectors were advanced to the 1.25 inch calibration mark, another 10 to the 1.50 inch mark, and the remaining 10 to the 1.75 inch mark. The load on the heat seal of each collector under stretched condition was calculated in pounds per inch of circumferential width. Immediately following removal of a collector from the mandrel, the diameter of the opening was measured (at time $T_o$), to determine the extent of immediate elastic recovery, and the measurement was repeated 10 minutes later (at $T_{10}$).

The following data setting forth the average values for each of the three batches of samples was tabulated as follows:

| | | | $T_0$ (time) | | $T_{10}$ (time) | |
|---|---|---|---|---|---|---|
| Original Diameter | Stretched Test Diameter | % Increase in Diameter | Diameter (avg.) | % Recovery (avg.) | Diameter (avg.) | % Recovery |
| 1.00" | 1.25" | 25% | 1.04" | 21% | 1.01" | 24% |
| 1.00" | 1.50" | 50% | 1.11" | 39% | 1.06" | 44% |
| 1.00" | 1.75" | 75% | 1.28" | 47% | 1.14" | 61% |

It is believed that even greater percentages of elastic recovery would be obtainable if the pouches had been formed of a polymeric film having a greater modulus of elasticity, but the data reveals a sufficiently high degree of stretchability in the heat seal area surrounding the collector opening, at a sufficiently low force or load and with high enough recovery for accomplishing the purposes of this invention.

Figure 6:
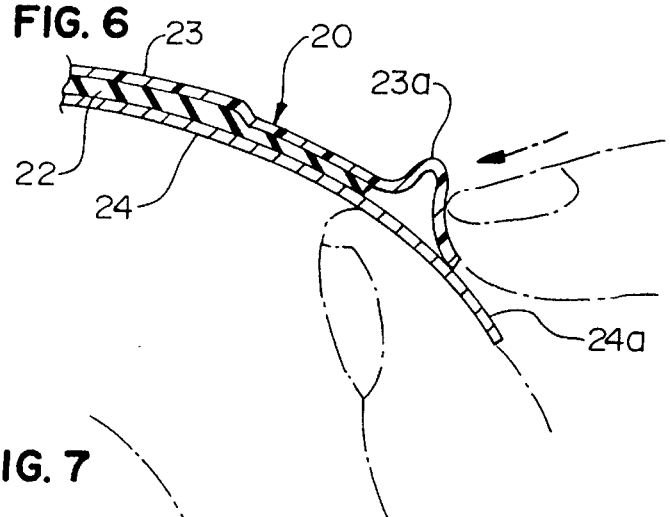
FIG. 6 is a fragmentary sectional view illustrating a procedure for separating the tab portions of the backing layer and release sheet just prior to removal of the release sheet.

Referring again to the drawings, it will be observed that both the cover layer 23 and the release sheet 24 have tab portions 23a and 24a that extend radially outwardly beyond the periphery of skin barrier layer 22 (FIG. 2). The purpose of tab portion 24a is to provide gripping means to be used by a nurse or other careprovider for peeling the release sheet 24 away from the adhesive surface of skin barrier layer 22. In the preferred embodiment, the two tab portions overlie each other and their opposing surfaces may be (and would normally be) in non-adhesive contact. Since the tab portions are of identical size and shape (preferably having been simultaneously die cut during manufacture of the patch 20), separating them for purposes of grasping tab portion 24a and commencing removal of the release sheet might be considered troublesome were it not for the fact that backing layer 23 is soft and flexible, and release sheet 24 has a slippery non-sticking surface facing barrier layer 22. Thus, separation of tab portions 23a and 24a may be easily commenced simply by sliding and buckling tab portion 23a as depicted in FIG. 6. At that point, the tab portions are sufficiently separated so that portion 24a may be easily grasped and the release sheet may be removed.

Figure 7:
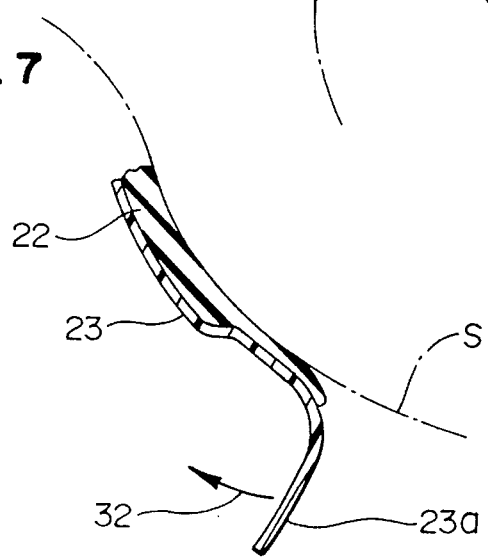
FIG. 7 is a fragmentary sectional view illustrating how the tab of the backing layer is utilized to commence removal of the adhesive patch from its attachment to a patient.

The tab portion 23a of the backing layer is important because it provides gripping means for removing the collector from the perianal skin surfaces after a period of wear. During that period, the barrier 23 will have absorbed moisture from the skin as well as from fluids discharged into the pouch and, being viscous elastic in character with fluid retained by the swollen hydrocolloids, some limited outward migration of the barrier material tending to obscure the sharpness of its outer margin may have occurred. Also, the fluid absorbed by the barrier tend to reduce its cohesiveness and inner strength, all of which would make it more difficult to peel the barrier away from the skin if it were not for the tab portion 23a of cover layer 23. Since even after a period of use of the fecal collector, the adhesive attachment between cover layer 23 and barrier layer 22 is in most cases stronger than the adhesive attachment between the hydrated barrier layer 22 and skin surface S, a pulling force exerted on tab portion 23 in the direction of arrow 32 in FIG. 7 causes the barrier material to peel away from the skin and greatly facilitate removal of the entire fecal collecting appliance.

The appliance is constructed and arranged so that a portion or section of the patch is intended to cover the perineal skin surfaces when the pouch is properly applied. The perineal-covering zone of the patch is generally indicated by phantom lines 33 in FIG. 4. When the appliance is worn by a female patient, the outer margin of the patch between lines 33 faces in the direction of the vaginal introitus. A minor proportion of female patients, estimated at being about 30 percent, have a perineal dimension less than the preferred radial dimension between the inner and outer margins of the patch. For example, if the patch 20 has a preferred outer diameter within the range of 3 to 4 inches, the patch will fit the great majority of female wearers (about 60 percent) without the patch covering any portion of the introitus. The central location of the patch opening and the large size of the patch assures a large area of adhesive contact with the patient not only in the perineal area (a particularly difficult area to secure effective adhesive attachment) but in an area extending 360 degrees about the opening. For the smaller number of female patients for which the perineal-covering dimension of the patch is too large, the careprovider may easily tailor the patch to suit the needs of a given patient by cutting (with scissors) and removing a peripheral section of the perineal-covering portion of the patch. Guidelines 34 imprinted on the release sheet 24 indicate the maximum limits of the section to be removed and, as revealed in FIG. 4, suitable instructions 35 may be imprinted on the release sheet to warn the user not to cut beyond the guidlines. The largest section that may be removed is represented in FIGS. 3 and 4 by numeral 36 and, while the area is shown to be generally triangular in shape, it should be understood that guidelines 34 simply set the outer limits for cutting and that removal of a section of maximum size, or one necessarily of triangular shape, would not be required.

While in the foregoing I have disclosed an embodiment of the invention in considerable detail for purposes of illustration, it will be understood by those skilled in the art that many of these details may be varied without departing from the spirit and scope of the invention.

I claim:

1. A fecal collector comprising a bag of elastomeric heat-sealable film having an opening for receiving fecal discharge; a thin annular attachment patch having a central opening in register with the opening of said bag; said patch comprising a skin barrier layer of rubbery pressure-sensitive adhesive having liquid-absorbing hydrocolloid particles dispersed therein and having a backing layer secured to one side of said skin barrier layer; said backing layer being formed of flexible, stretchable and contractable heat-sealable material and being joined to said bag along a narrow heat seal line immediately surrounding said opening of said bag and patch; said openings of said bag and patch being expandable and contractable, and said patch and bag being stretchable and recoverable, to conform with changes in size and shape of perianal surfaces during evacuation; and a flexible but substantially non-stretchable release sheet removably attached to the side of said adhesive layer opposite from said backing layer and carrying guidelines outlining a removable perineal section extending from the outer periphery of said patch and terminating inwardly at a point spaced from the central opening of said patch; said guidelines defining a section of generally triangular shape.

2. A fecal collector comprising a bag of heat-sealable film having an opening for receiving fecal discharge; a thin annular attachment patch having a central opening in register with the opening of said bag; said patch comprising a skin barrier layer of rubbery pressure-sensitive adhesive having liquid-absorbing hydrocolloid particles dispersed therein and having a backing layer secured to one side of said skin barrier layer; said backing layer being formed of flexible, stretchable and contractable heat-sealable material and being joined to said bag along a narrow heat seal line surrounding said opening of said bag and patch; and a flexible but substantially non-stretchable release sheet removably attached to the side of said adhesive layer opposite from said backing layer and carrying guidelines outlining a removable perineal section extending from the outer periphery of said patch and terminating inwardly at a point spaced from the central opening of said patch; said guidelines defining a section of generally triangular shape.

3. A fecal collector comprising a bag of elastomeric heat-sealable film having an opening for receiving fecal discharge; a thin annular attachment patch having a central opening in register with the opening of said bag; said patch comprising a skin barrier layer of rubber pressure-sensitive adhesive having liquid-absorbing hydrocolloid particles dispersed therein and having a backing layer secured to one side of said skin barrier layer; said backing layer being formed of flexible, stretchable and contractable heat-sealable material and being joined to said bag along a narrow heat seal line immediately surrounding said openings of said bag and patch; said openings of said bag and patch being expandable and contractable, and said patch and bag being stretchable and recoverable, to conform with changes in size and shape of perianal surfaces during evacuation; said openings of said bag and patch being of equal size within the range of 0.5 to 1.5 inches in diameter when said bag and patch are unstretched; said attachment patch having an outer margin concentric with the opening thereof with at least 80% of the adhesive area of said patch being disposed between said heat seal line and said outer margin; and a flexible but substantially non-stretchable release sheet being removably attached to the side of said adhesive layer opposite from said backing layer; said release sheet carrying guidelines outlining a removable perineal section extending from the outer periphery of said patch and terminating inwardly at a point spaced from the peripheral opening of said patch.

4. The collector of claim 3 in which said guidelines define a section of generally triangular shape.

\* \* \* \* \*